US012702618B2

(12) United States Patent
Tass

(10) Patent No.: US 12,702,618 B2
(45) Date of Patent: Aug. 11, 2026

(54) SYSTEMS AND METHODS FOR NEUROFEEDBACK-TRIGGERED THERAPY FOR NEUROLOGICAL CONDITIONS

(71) Applicant: The Board of Trustees of the Leland Stanford Junior University, Stanford, CA (US)

(72) Inventor: Peter A. Tass, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 856 days.

(21) Appl. No.: 17/906,255

(22) PCT Filed: Mar. 15, 2021

(86) PCT No.: PCT/US2021/022427
§ 371 (c)(1),
(2) Date: Sep. 13, 2022

(87) PCT Pub. No.: WO2021/184019
PCT Pub. Date: Sep. 16, 2021

(65) Prior Publication Data

US 2023/0131710 A1 Apr. 27, 2023

Related U.S. Application Data

(60) Provisional application No. 62/989,509, filed on Mar. 13, 2020.

(51) Int. Cl.
*A61H 23/02* (2006.01)
*A61B 5/00* (2006.01)
(Continued)

(52) U.S. Cl.
CPC ............ *A61H 23/02* (2013.01); *A61B 5/383* (2021.01); *A61B 5/384* (2021.01); *A61B 5/4836* (2013.01);
(Continued)

(58) Field of Classification Search
CPC ...... A61H 23/00–06; A61H 2201/1635; A61H 2201/5005; A61H 2201/5043;
(Continued)

(56) References Cited

U.S. PATENT DOCUMENTS

2002/0095076 A1* 7/2002 Krausman .......... A61B 5/14552 600/323
2012/0226185 A1* 9/2012 Chung .................. A61B 5/374 600/544

(Continued)

FOREIGN PATENT DOCUMENTS

WO 2011127917 A2 10/2011
WO WO-2019023467 A1 * 1/2019 ............... A61H 1/00
WO 2021184019 A1 9/2021

OTHER PUBLICATIONS

International Preliminary Report on Patentability for International Application PCT/US2021/022427, Report issued Sep. 6, 2022, Mailed on Sep. 22, 2022, 5 Pgs.

(Continued)

*Primary Examiner* — Paige Kathleen Bugg
(74) *Attorney, Agent, or Firm* — KPPB LLP

(57) ABSTRACT

Systems and methods for neurofeedback-triggered therapy for neurological conditions in accordance with embodiments of the invention are illustrated. One embodiment includes a neurofeedback-triggered therapy system, including a plurality of vibrotactile stimulators, a brain activity recorder, and a controller, including a processor, and a memory, the memory containing a neurofeedback application, where in (Continued)

order to condition a user to reduce the symptoms of a neurological condition on demand triggered by upregulating sensorimotor rhythm (SMR) activity, the neurofeedback application directs the processor to obtain brain activity data from the brain activity recorder, identify sensorimotor rhythm (SMR) spindles in the brain activity data, and provide vibrotactile Coordinated Reset (vCR) stimulation to a user using the plurality of vibrotactile stimulators when SMR spindles are identified, where the vCR stimulation reduces the symptoms of a neurological condition of the user.

20 Claims, 5 Drawing Sheets

(51) Int. Cl.
*A61B 5/383* (2021.01)
*A61B 5/384* (2021.01)

(52) U.S. Cl.
CPC ............ *A61B 5/6803* (2013.01); *A61B 5/742* (2013.01); *A61H 2201/1635* (2013.01); *A61H 2201/5005* (2013.01); *A61H 2201/5043* (2013.01); *A61H 2230/105* (2013.01)

(58) Field of Classification Search
CPC .. A61H 2230/105; A61B 5/372; A61B 5/316; A61B 5/369; A61B 5/4836; A61B 5/6803; A61B 5/742
USPC ........................................................... 601/46
See application file for complete search history.

(56) References Cited

U.S. PATENT DOCUMENTS

2012/0253163 A1* 10/2012 Afanasewicz ....... A61B 5/6814 600/383
2014/0316230 A1* 10/2014 Denison ................ A61B 5/168 600/545
2016/0067136 A1 3/2016 Raghavan et al.
2018/0140249 A1 5/2018 Frohlich
2020/0069208 A1* 3/2020 Keane .................... G16H 20/70
2021/0169417 A1* 6/2021 Burton ................. A61B 5/4857

OTHER PUBLICATIONS

International Search Report and Written Opinion for International Application No. PCT/US2021/022427, Search completed May 10, 2021, Mailed Jun. 3, 2021, 12 pgs.

Cook et al., "A Single Case Feasibility Study of Sensorimotor Rhythm Neurofeedback in Parkinson's Disease", Frontiers in Neuroscience, vol. 15, No. 623317, Feb. 2021, 9 pgs.

Kromer et al., "Long-lasting desynchronization by decoupling stimulation", Physical Review Research, vol. 2, No. 033101, Jul. 20, 2020, 20 pgs.

Pfeifer et al., "Coordinated Reset Vibrotactile Stimulation Induces Sustained Cumulative Benefits in Parkinson's Disease", Frontiers in Physiology, vol. 12, Apr. 5, 2021.

Tass et al., "Vibrotactile Coordinated Reset Stimulation for the Treatment of Neurological Diseases: Concepts and Device Specifications", Cureus, vol. 9, No. 8, Aug. 2, 2017, 12 pgs., DOI: 10.7759/cureus.1535.

Arns et al., "Efficacy of Neurofeedback Treatment in ADHD: The Effects on Inattention, Impulsivity and Hyperactivity: A Meta-Analysis", Clinical EEG and Neuroscience, vol. 40, No. 3, Jul. 1, 2009, https://doi.org/10.1177/155005940904000.

Doppelmayr et al., "Effects of SMR and Theta/Beta Neurofeedback on Reaction Times, Spatial Abilities, and Creativity", Journal of Neurotherapy, May 20, 2011, 10.1080/10874208.2011.570689.

Sterman et al., "Foundation and practice of neurofeedback for the treatment of epilepsy", Applied Psychophysiology and Biofeedback, vol. 31, No. 1, Mar. 2006.

Tan et al., "Meta-analysis of EEG biofeedback in treating epilepsy", Clinical EEG and Neuroscience, vol. 40, No. 3, Jul. 1, 2009, https://doi.org/10.1177/155005940904000310.

* cited by examiner

SYSTEMS AND METHODS FOR NEUROFEEDBACK-TRIGGERED THERAPY FOR NEUROLOGICAL CONDITIONS

CROSS-REFERENCE TO RELATED APPLICATIONS

The current application is a national stage application of PCT Application No. PCT/US2021/022427 entitled "Systems and Methods for Neurofeedback-Triggered Therapy for Neurological Conditions" filed Mar. 15, 2021 which claims the benefit of and priority under 35 U.S.C. § 119 (e) to U.S. Provisional Patent Application No. 62/989,509 entitled "Device and Procedure That Delivers Neuromodulation Triggered and Modulated by Neurofeedback" filed Mar. 13, 2020. The disclosures of PCT Application No. PCT/US2021/022427 and U.S. Provisional Patent Application No. 62/989,509 are hereby incorporated by reference in its entirety for all purposes.

FIELD OF THE INVENTION

The present invention generally relates to neurofeedback-triggered therapy for neurological conditions, namely inducing vibrotactile Coordinated Reset stimulation effects using sensory motor rhythm neurofeedback in patients having Parkinson's disease.

BACKGROUND

The sensorimotor rhythm (SMR, also referred to as "sensory motor" or "sensory-motor" rhythm) is a brain wave typically occurring in sensorimotor cortex at the 13-15 Hz frequency range. The SMR appears as a spindle in electroencephalography (EEG), magnetoencephalography (MEG), and electrocorticography (ECoG) measurements of the sensorimotor cortex. Neurofeedback is the presentation of real-time brain activity to a user in order to train the user to self-regulate brain activity. SMR can be upregulated via neurofeedback training (i.e. a user can learn to increase to number of spindles that occur in a given time period).

SUMMARY OF THE INVENTION

Systems and methods for neurofeedback-triggered therapy for neurological conditions in accordance with embodiments of the invention are illustrated. One embodiment includes a neurofeedback-triggered therapy system, including a plurality of vibrotactile stimulators, a brain activity recorder, and a controller, including a processor, and a memory, the memory containing a neurofeedback application, where in order to condition a user to reduce the symptoms of a neurological condition on demand triggered by upregulating sensorimotor rhythm (SMR) activity, the neurofeedback application directs the processor to obtain brain activity data from the brain activity recorder, identify sensorimotor rhythm (SMR) spindles in the brain activity data, and provide vibrotactile Coordinated Reset (vCR) stimulation to a user using the plurality of vibrotactile stimulators when SMR spindles are identified, where the vCR stimulation reduces the symptoms of a neurological condition of the user.

In another embodiment, the brain activity recorder is an electroencephalogram (EEG) machine.

In a further embodiment, the EEG machine is integrated into a headwear.

In still another embodiment, the neurological condition is selected from the group consisting of: Parkinson's disease, essential tremor, dystonia, epilepsy, dysfunction after stroke, obsessive-compulsive disorder, Tourette syndrome, dementia, and complex regional pain syndrome.

In a still further embodiment, the plurality of vibrostimulators comprises eight vibrostimulators, where each stimulator is uniquely placed on the fingertips of an index, middle, ring, and pinky fingers of a right and a left hand of the user.

In yet another embodiment, the vCR stimulation is provided in a wave-inducing stimulation sequence.

In a yet further embodiment, the neurofeedback application further directs the processor to introduce a shift into the wave-inducing stimulation sequence after a predetermined number of stimulation cycles.

In another additional embodiment, the system further includes a display, where the neurofeedback application further directs the processor to provide visual feedback via the display.

In a further additional embodiment, the visual feedback includes a point counter, where the point counter increments upon identification of an SMR spindle.

In another embodiment again, the neurofeedback application further directs the processor to provide audio feedback via a speaker.

In a further embodiment again, a method for neurofeedback-triggered therapy, including conditioning a user to reduce the symptoms of a neurological condition on demand triggered by upregulating sensorimotor rhythm (SMR) activity by obtaining brain activity data from a brain activity recorder, identifying sensorimotor rhythm (SMR) spindles in the brain activity data, and providing vibrotactile Coordinated Reset (vCR) stimulation to a user using a plurality of vibrotactile stimulators when SMR spindles are identified, where the vCR stimulation reduces the symptoms of the neurological condition of the user.

In still yet another embodiment, the brain activity recorder is an electroencephalogram (EEG) machine.

In a still yet further embodiment, the EEG machine is integrated into a headwear.

In still another additional embodiment, the neurological condition is selected from the group consisting of: Parkinson's disease, essential tremor, dystonia, epilepsy, dysfunction after stroke, obsessive-compulsive disorder, Tourette syndrome, dementia, depression, and complex regional pain syndrome.

In a still further additional embodiment, the plurality of vibrostimulators includes eight vibrostimulators, where each stimulator is uniquely placed on the fingertips of an index, middle, ring, and pinky fingers of a right and a left hand of the user.

In still another embodiment again, the vCR stimulation is provided in a wave-inducing stimulation sequence.

In a still further embodiment again, the method further includes introducing a shift into the wave-inducing stimulation sequence after a predetermined number of stimulation cycles.

In yet another additional embodiment, the method further includes providing visual feedback via a display.

In a yet further additional embodiment, the visual feedback comprises a point counter, where the point counter increments upon identification of an SMR spindle. In yet another embodiment again, the method further includes providing audio feedback via a speaker.

In a yet further embodiment again, a neurological conditioning system comprising a glove comprising a plurality of vibrotactile stimulators, an EEG headset, and a controller, wherein the controller obtains brain activity data from the EEG headset, identifies SMR spindles in the brain activity data, delivers vCR stimulation to a user via the plurality of vibrotactile stimulators, and provides visual feedback via a display, the visual feedback comprising a point counter that increments each time an SMR spindle is detected.

In another additional embodiment again, the controller is a smartphone.

In a further additional embodiment again, the controller provides audio feedback.

In still yet another additional embodiment, the visual feedback comprises a game.

In another yet additional embodiment, a neurofeedback-triggered therapy system, includes a plurality of stimulators, a brain activity recorder, and a controller configured to condition a user to reduce the symptoms of a neurological condition on demand triggered by upregulating sensorimotor rhythm (SMR) activity, where the controller obtains brain activity data from the brain activity recorder, identifies sensorimotor rhythm (SMR) spindles in the brain activity data, and provides stimulation to a user using the plurality of stimulators when SMR spindles are identified, where the stimulation is configured to treat the symptoms of a neurological condition.

In another yet additional embodiment again, the brain activity recorder is an electroencephalogram (EEG) machine.

In still another yet additional embodiment again, the stimulation is Coordinated Reset stimulation delivered using a stimulation mechanism selected from the group consisting of: vibrotactile stimulation, acoustic stimulation, visual stimulation, thermal stimulation, transcutaneous electrical stimulation, transcranial electrical stimulation, and transcranial magnetic stimulation.

In a still yet another additional embodiment again, the stimulation is configured to treat the symptoms of a neurological condition by desynchronizing abnormal synchronizations in the user's brain, and the neurological condition is selected from the group consisting of: Parkinson's disease, essential tremor, dystonia, epilepsy, dysfunction after stroke, obsessive-compulsive disorder, Tourette syndrome, dementia, depression, and complex regional pain syndrome.

Additional embodiments and features are set forth in part in the description that follows, and in part will become apparent to those skilled in the art upon examination of the specification or may be learned by the practice of the invention. A further understanding of the nature and advantages of the present invention may be realized by reference to the remaining portions of the specification and the drawings, which forms a part of this disclosure.

BRIEF DESCRIPTION OF THE DRAWINGS

The description and claims will be more fully understood with reference to the following figures and data graphs, which are presented as exemplary embodiments of the invention and should not be construed as a complete recitation of the scope of the invention.

DETAILED DESCRIPTION

Figure 1:
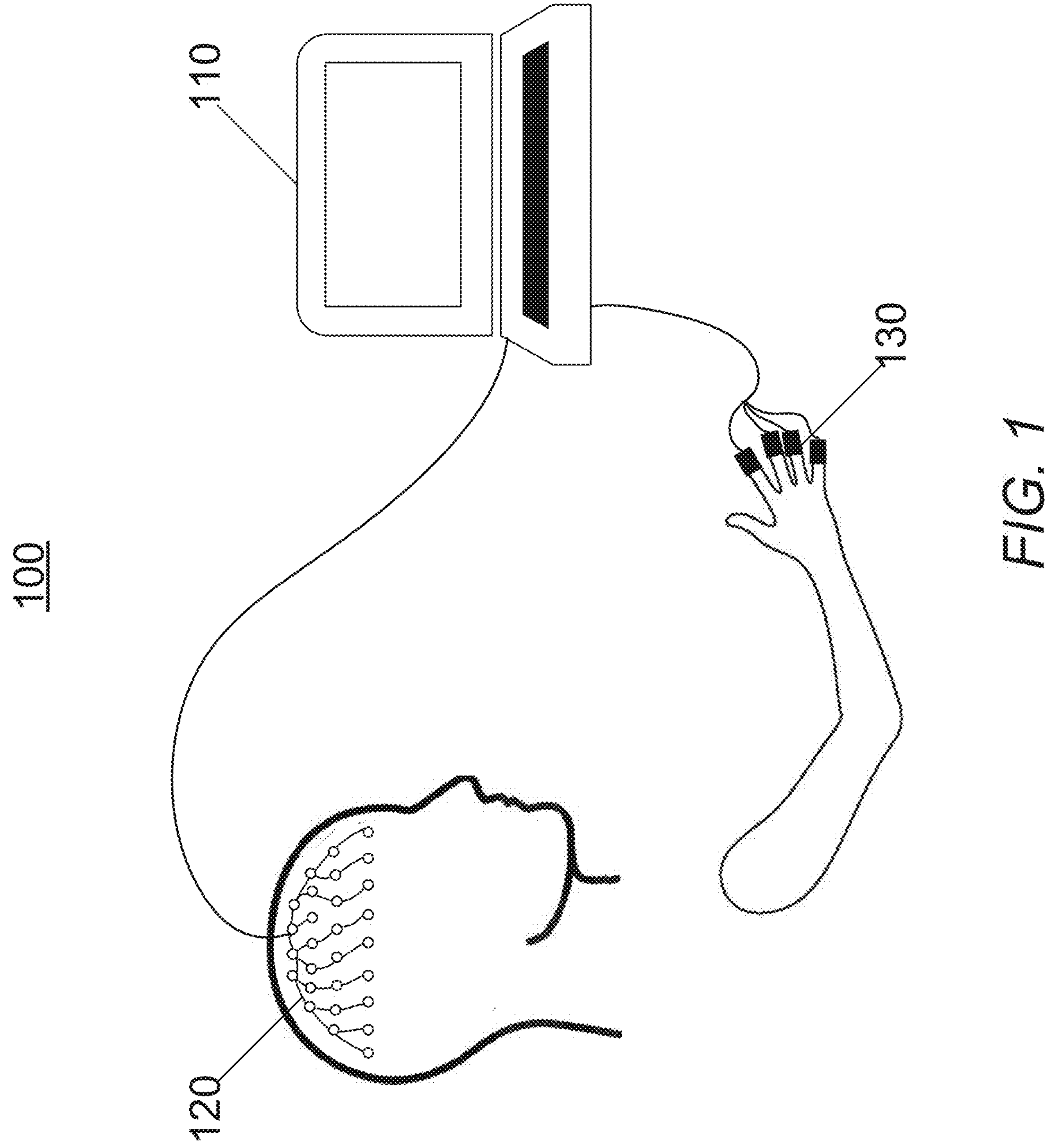
FIG. 1 illustrates a neurofeedback-triggered therapy system in accordance with an embodiment of the invention.

Parkinson's disease is a neurological condition characterized by impaired sensorimotor integration, i.e. the matching of sensory feedback (from the periphery) and motor outputs. While there is currently no known cure, conventional treatments include medication with L-DOPA or other pharmaceuticals, and when symptoms worsen to a significant degree, deep brain stimulation (DBS). One type of stimulation that can be provided via DBS is Coordinated Reset (CR) stimulation. CR stimulation attempts to desynchronize abnormal synchrony in the brain in order to alleviate symptoms of Parkinson's disease. Recently, it has been shown that CR stimulation can be delivered via vibration applied to the fingertips without the need for invasive DBS implants. This vibrotactile Coordinated Reset (vCR) stimulation can be applied using one or more vibration units such as, but not limited to, piezo actuators or other mechanical stimulators.

An obvious problem with conventional CR delivered via DBS is that it requires an invasive surgery involving implantation of electrical stimulators into the brain. While vCR is significantly less invasive, it can be time consuming for patients to realize benefit as the stimulation must be applied often and for long periods of time. In many cases, users must use vCR for 2-4 hours per day during at least the first 4-6 months of treatment. During application of vCR, the patient is hooked up to the vibration units which reduces their ability to use their hands. In order to provide the benefits of vCR without the constant need to set up and use vibration units, systems and methods described herein utilize training devices which modify the user's brain to produce the effects of vCR without actually receiving stimulation by neurologically pairing the effects to upregulation of sensorimotor rhythm (SMR).

Turning now to the drawings, systems and methods for neurofeedback-triggered therapy for neurological conditions are described. Neurofeedback training can be used to teach an individual to consciously upregulate the frequency of SMR spindles. Training devices described herein can induce a conditioned response to the upregulation that produces the effects of vCR without the presence of vCR stimulators. In many embodiments, an EEG or similar brain activity recording device is used to record brain activity of a user (e.g. neural oscillations or "brain waves"). SMR spindles are identified in the brain activity, and each time a spindle is detected, vCR stimulation can be provided in near real time to the user via a connected vCR stimulator. The training device can present a gamified experience to the user that incentivizes them to increase the number of SMR spindles (e.g. via accumulation of points or other, more complex game mechanics). In many embodiments, after sufficient use, a user will be able to upregulate their SMR activity without the training device and trigger the beneficial effects of vCR stimulation without needing to use a vCR stimulator.

In many embodiments, systems and methods described herein operate using methods similar to those of classical conditioning. To this end, the non-invasive neuromodulation (e.g. vCR) can be treated as conditioned stimulus, whereas the neurofeedback (e.g. visual feedback, audio feedback, and/or any other feedback as appropriate to the requirements of specific applications of embodiments of the invention) is treated as the unconditioned stimulus. In many embodiments, the unconditioned stimulus occurs between 0.1 seconds and 1 minute (or even up to 5 minutes) before or during the conditioned stimulus. Thus the conditioned stimulus acts as a type of signal or cue for the unconditioned stimulus.

In various embodiments, the duration of the non-invasive neuromodulation stimulus session may be constant, e.g. between 5 and 30 minutes. Alternatively, in various embodiments, the duration of the session may depend on the performance of the user, i.e. the extent that SMR exceeds the detection threshold. The duration of the presentation of the visual (non-neuromodulation) feedback cues can be standard. For instance, bars on a visual display the amount of SMR (averaged in a reasonable time window) in a close-to online manner, whereas e.g. reward-type of (visually displayed) points remain on the screen during the neurofeedback session. While systems and methods that use vCR as the stimulation method are described herein, alternative non-invasive neurostimulation methods can be integrated or replace the vCR without departing from the scope or spirit of the invention. For example, in many embodiments, sensory CR stimulation (not only vibrotactile CR stimulation), e.g. acoustic or visual or thermal or transcutaneous electrical or transcranial electrical or transcranial magnetic CR stimulation, or combinations thereof can be delivered. Additionally, any non-invasive stimulation that delivers long-lasting therapeutic effects can be used as a replacement for vCR. Systems for neurofeedback-triggered therapy are described in further detail below.

Neurofeedback-Triggered Therapy Systems

Neurofeedback-triggered therapy systems can be used to induce a conditioned response to SMR upregulation. In many embodiments, the induced response is desynchronization of abnormal synchrony in the brain, such as (but not limited to) Parkinsonian abnormal synchronies. In many embodiments, neurofeedback-triggered therapy systems are portable and include various connected components including vCR stimulators, a brain activity recorder, and a controller. In various embodiments, between 1 and 10 vCR stimulators are included, where one is used per finger. However, in many embodiments, additional vCR stimulators can be used on different parts of the body. Not every finger needs to have a vCR stimulator. In many embodiments, stimulators can be incorporated into a piece of clothing such as (but not limited to) bands and gloves. Brain activity recorders can be portable recorders such as (but not limited to) EEG headsets or cap (collectively “headwear”). These headsets can be constructed in such a way as to be embedded in hats or other cosmetically appealing forms. The brain activity recorder can produce brain activity data which is in turn provided to the controller. When the controller detects an SMR spindle, it can trigger vCR stimulation via the vCR stimulators.

In many embodiments, the controller is further connected to (or integrated into) a display. The display can be used to provide visual and/or auditory feedback to the user about the detection of SMR spindles. In many embodiments, a point counter is provided which increases for every detected SMR spindle. In various embodiments, a “spindles per minute” counter is provided. Other counters or game metrics can be provided such as (but not limited to) high scores representing the most SMR spindles detected in a given period, a virtual game environment with characters, objects, and/or avatars that respond to the detection of SMR spindles, or any other gamification as appropriate to the requirements of specific applications of embodiments of the invention. In numerous embodiments, the controller is a smartphone. However, the controller can be a personal computer, a tablet computer, a purpose-built device, or any other computing device as appropriate to the requirements of specific applications of embodiments of the invention.

Turning now to FIG. 1, a neurofeedback-triggered therapy system in accordance with an embodiment of the invention is illustrated. Neurofeedback-triggered therapy system 100 includes a controller 110. The controller 110 is connected to brain activity recorder 120 and vCR stimulators 130. While a particular neurofeedback-triggered therapy system in accordance with an embodiment of the invention is illustrated in FIG. 1, as can be readily appreciated any number of different system architectures can be used including (but not limited to), those with different numbers of vCR stimulators, those using wireless connections between different components, different controllers (e.g. smartphones, etc.) and/or different types of brain activity recorders such as (but not limited to) ECoG, or MEG.

Figure 2:
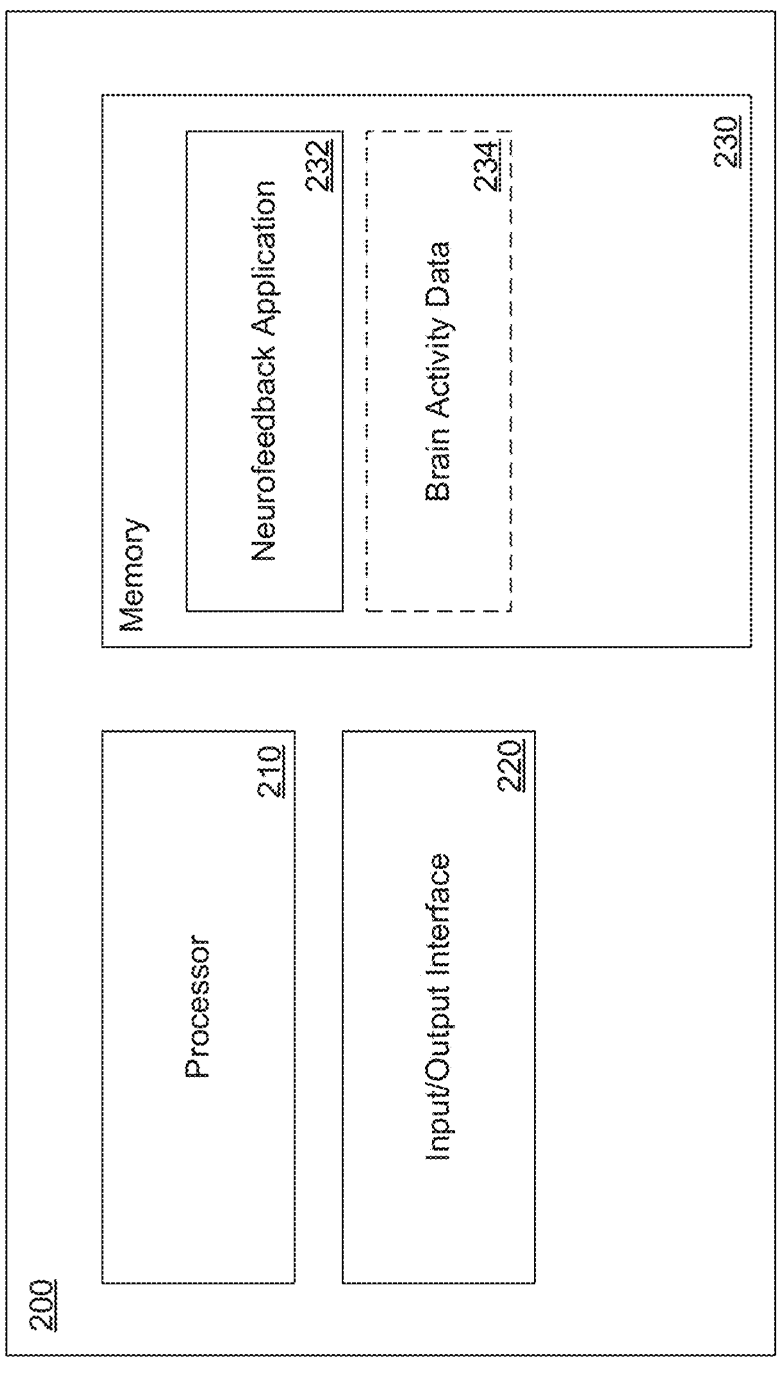
FIG. 2 illustrates a block diagram for a controller in accordance with an embodiment of the invention.

Turning now to FIG. 2, a block diagram for a controller in accordance with an embodiment of the invention is illustrated. Controller 200 includes a processor 210. In many embodiments, the processor is a logic circuit capable of executing instructions such as (but not limited to) a central processing unit (CPU), a graphics processing unit (GPU), a field programmable gate array (FPGA), an application-specific integrated circuit (ASIC), and/or any combination thereof. In many embodiments, more than one processor can be used. The controller 200 further includes an input/output (I/O) interface 220. The I/O interface can be used to communicate with different components such as (but not limited to) displays, speakers, brain activity recorders, vCR stimulators, and/or any other component via wired or wireless connections.

The controller 200 further includes a memory 230. The memory 230 can be made of volatile memory, nonvolatile memory, or any combination thereof. The memory 230 contains a neurofeedback application 232. The training application can direct the processor to carry out neurofeedback-triggered therapy processes. In many embodiments, the memory 230 further contains brain activity data obtained from brain activity recorders. Brain activity data can describe brain activity as a signal or set of signals. As can be readily appreciated, controllers can be manufactured in different ways using similar computing components without departing from the scope or spirit of the invention. Neurofeedback-triggered therapy processes are discussed in further detail below.

Neurofeedback-Triggered Therapy Processes

Neurofeedback can be used to train an individual to upregulate SMR activity. Systems described herein can be used to condition an individual to feel the benefits of vCR therapy when they upregulate their SMR activity. In this way, even when vCR stimulators are not used, desynchronization of abnormal synchronizations can be achieved on demand. This can ameliorate some symptoms of Parkinson’s disease or other neurological conditions (e.g. essential tremor and other movement disorders, dystonia, epilepsy, dysfunction after stroke, obsessive-compulsive disorder (OCD), Tourette syndrome, dementia, depression, complex regional pain syndrome, and other neurological conditions) in a quick, effective manner that can later be exercised at any time without the use of the systems described herein.

Figure 3:
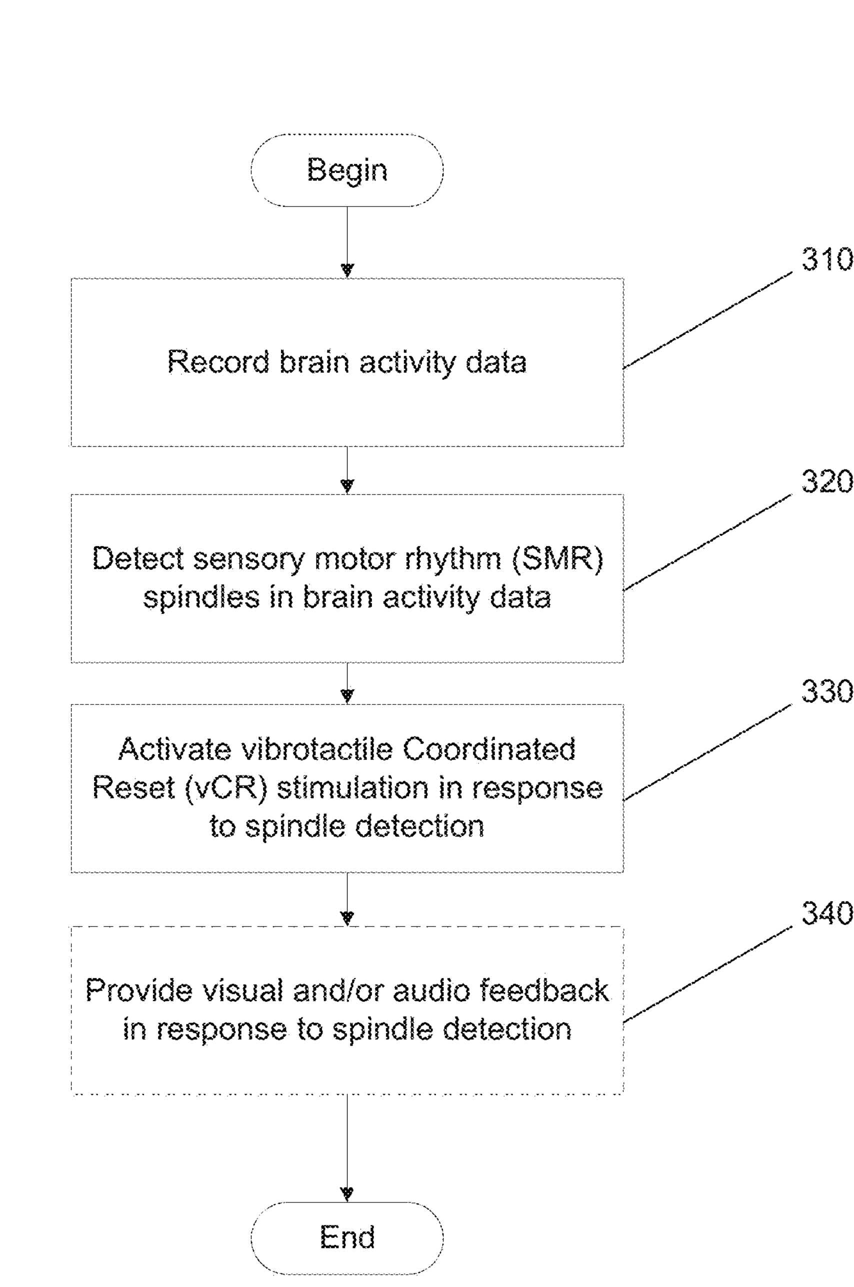
FIG. 3 conceptually illustrates a process for neurofeedback-triggered therapy in accordance with an embodiment of the invention.

Turning now to FIG. 3, a neurofeedback-triggered therapy process for conditioning an individual using a neurofeedback-triggered therapy system in accordance with an embodiment of the invention is illustrated. Process 300 includes recording (310) brain activity data of a user using a brain activity recorder. In many embodiments, the brain activity recorder is an EEG, and the brain activity data is one or more EEG signals. SMR spindles are detected (320) in the brain activity data. When an SMR spindle is detected, vCR stimulators are activated (330) to provide vCR stimulation in response. In many embodiments, audio and/or visual feedback is provided (340) in response to the detection as well in order to encourage the user to continue to attempt to increase the number of SMR spindles. However, visual and/or audio feedback is not a requirement, nor is any kind of display.

In various embodiments, directions as to how to upregulate SMR activity can be provided via a display. While each person tends to be idiosyncratic in their exact personal method of upregulation, general advice such as "imagine yourself moving," "imagine flapping your arms like wings to fly," and so on can be provided. In numerous embodiments, gamification elements can be presented to the user as further encouragement and feedback. As can be readily appreciated, any number of different audio/visual feedback elements can be provided without departing from the scope or spirit of the invention. For many users, after sufficient conditioning, attempting to upregulate their SMR activity will trigger the effects of vCR.

Figure 4:
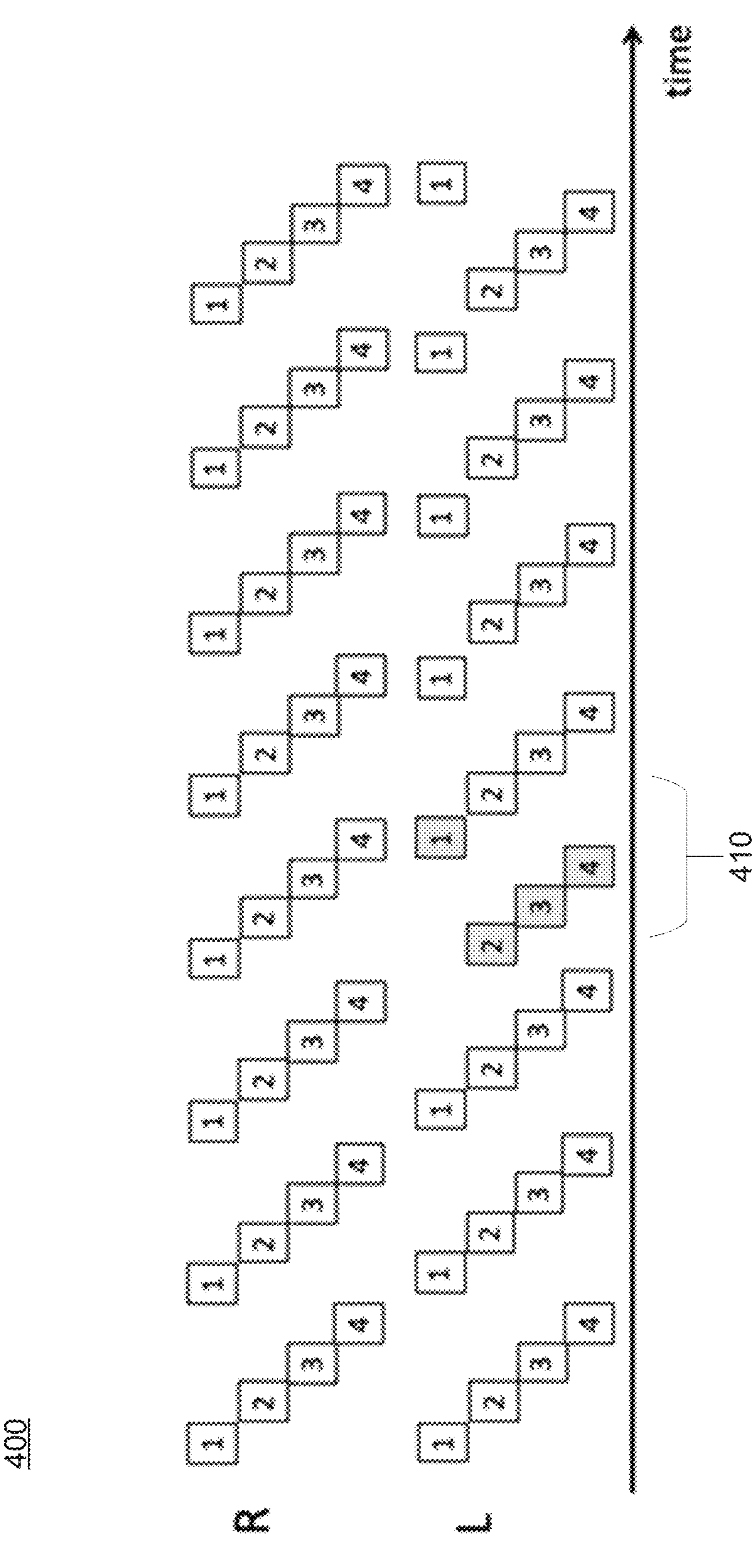
FIG. 4 illustrates a vCR stimulation pattern in accordance with an embodiment of the invention.
Figure 5:
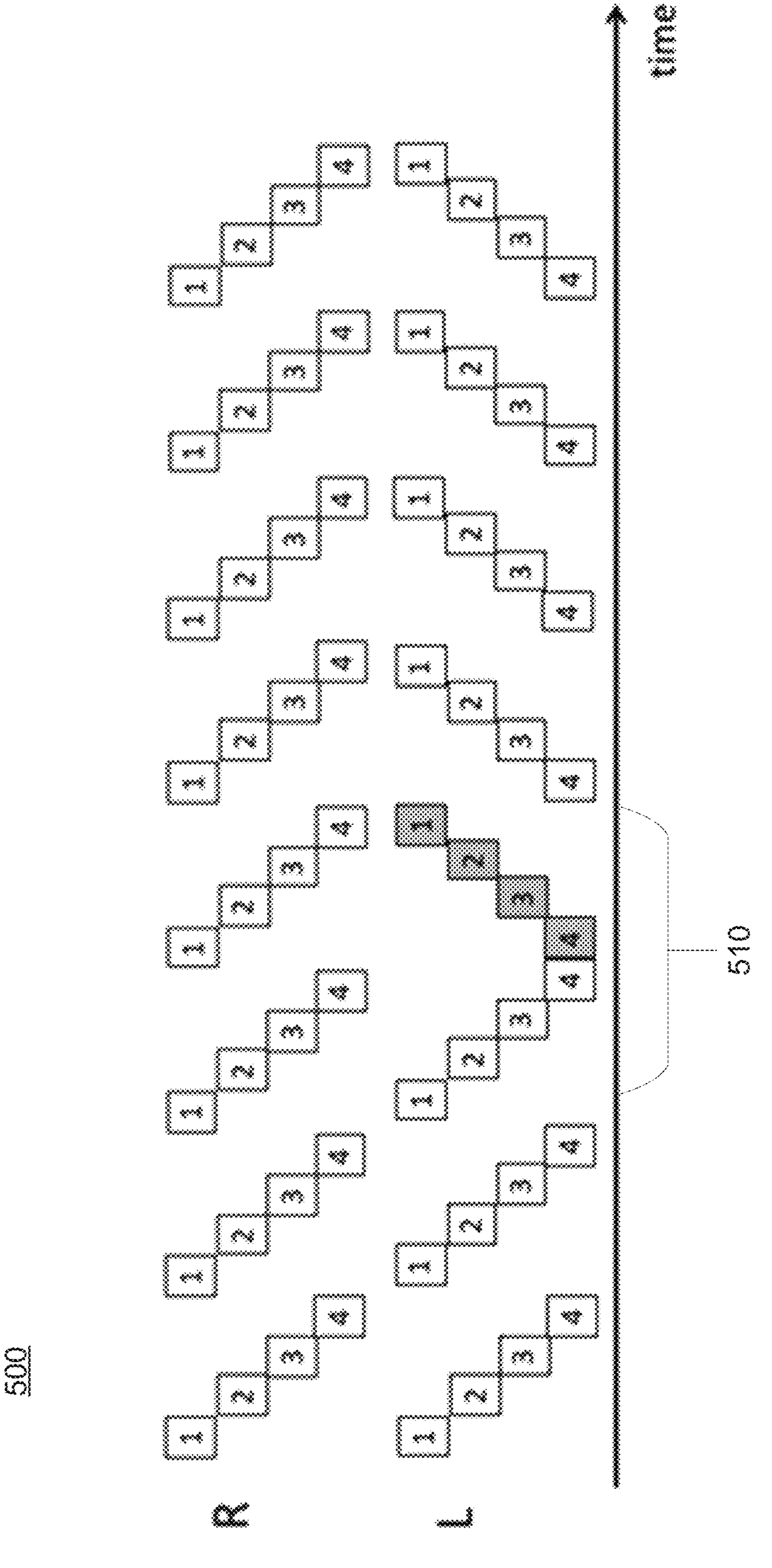
FIG. 5 illustrates a vCR traveling wave-inducing stimulation sequence

There are different types of vCR (and CR generally) patterns that can be used to desynchronized abnormal synchronizations. In numerous embodiments, the vCR stimulation pattern delivered to the user is preset. In various embodiments, the stimulation pattern is selected from a number of preset patterns. Patterns can be updated via provision of new data to the controller. Let the stimulation pattern sequence being delivered to the right fingers 1,2,3, 4,5 (or 1,2,3,4; 1,2,3; or any subset of fingers) be denoted as by SR. Analogously, denote the stimulation pattern being delivered to the left fingers as SL. SR and SL can be identical, e.g. 1-2-3-4, periodically delivered vibration cycle by cycle. Motivated to induce traveling activation patterns in the brain targets affected by the vibrotactile stimulation, the sequence 1-2-3-4 or the sequence 4-3-2-1 can be delivered to both hands. After 30 or 100 or more repetition, synchronous sequences delivered to both hands may be changed, e.g. by introducing a "jump", i.e. by omitting one or more fingers and continuing the periodically delivery of the mutually shifted sequence. The jump 410 can be seen in a portion of a stimulation pattern 400 in FIG. 4. Similar to a jump, in various embodiments, traveling wave-inducing stimulation sequences can shift directions as illustrated in FIG. 5. The shift 510 can be seen in a portion of a traveling wave-inducing stimulation sequence 500.

Travelling waves of activity can induce corresponding synaptic connectivity patterns. Purposefully introducing perturbations by inducing mutually shifted travelling waves in time with stimulation sequences such as those illustrated in FIG. 4, or reversing direction of the travelling wave in one of the brain targets with stimulation sequences such as those shown in FIG. 5, can induce an effective decrease of abnormal synaptic connectivity. While particular vCR patterns are discussed above, any number of different vCR patterns can be used as appropriate to the requirements of specific applications of embodiments of the invention. Further, as noted above, stimulation patterns can be specific to the type of stimulation mechanism (e.g. magnetic, electric, vibrational, thermal, acoustic, etc.), and may be used depending on the type of stimulation mechanism used as appropriate to the requirements of specific applications of embodiments of the invention.

Although specific methods of neurofeedback-triggered therapy are discussed above, many different methods can be implemented in accordance with many different embodiments of the invention. It is therefore to be understood that the present invention may be practiced in ways other than specifically described, without departing from the scope and spirit of the present invention. Thus, embodiments of the present invention should be considered in all respects as illustrative and not restrictive. Accordingly, the scope of the invention should be determined not by the embodiments illustrated, but by the appended claims and their equivalents.

What is claimed is:

1. A neurofeedback-triggered therapy system for reducing symptoms of a neurological condition of a user, comprising:
- a plurality of vibrotactile stimulators;
- a brain activity recorder; and
- a controller, comprising:
  - a processor; and
  - a memory, the memory containing a neurofeedback application,
  - wherein the neurofeedback application is configured to direct the processor to:
  - obtain brain activity data from the brain activity recorder;
  - identify sensorimotor rhythm (SMR) spindles in the brain activity data; and
  - responsive to identification of the SMR spindles, provide a therapeutic stimulation with a therapeutic effect to the user,
  - wherein the therapeutic stimulation comprises vibrotactile Coordinated Reset (vCR) stimulation using the plurality of vibrotactile stimulators,
  - wherein the vCR stimulation is configured to reduce the symptoms of the neurological condition of the user by desynchronizing abnormal synchrony in the user's brain; and
  - whereby the vCR stimulation is configured to condition the user to consciously upregulate a frequency of the SMR spindles to induce desynchronization of abnormal synchrony during a subsequent period without the vCR stimulation.

2. The neurofeedback-triggered therapy system of claim 1, wherein the brain activity recorder is an electroencephalogram (EEG) machine.

3. The neurofeedback-triggered therapy system of claim 2, wherein the EEG machine is integrated into a headwear.

4. The neurofeedback-triggered therapy system of claim 1, wherein the neurological condition is selected from the group consisting of: Parkinson's disease, essential tremor, dystonia, epilepsy, dysfunction after stroke, obsessive-compulsive disorder, Tourette syndrome, dementia, depression, and complex regional pain syndrome.

5. The neurofeedback-triggered therapy system of claim 1, wherein the plurality of vibrotactile stimulators comprises eight vibrotactile stimulators, where each vibrotactile stimulator is configured to be uniquely placed on fingertips of an index finger, a middle finger, a ring finger, and a pinky finger of a right and a left hand of the user.

6. The neurofeedback-triggered therapy system of claim 5, wherein the vCR stimulation is provided in a wave-inducing stimulation sequence.

7. The neurofeedback-triggered therapy system of claim 6, wherein the neurofeedback application is further configured to direct the processor to introduce a shift into the wave-inducing stimulation sequence after a predetermined number of stimulation cycles.

8. The neurofeedback-triggered therapy system of claim 1, further comprising a display, where the neurofeedback application is further configured to direct the processor to provide visual feedback via the display.

9. The neurofeedback-triggered therapy system of claim 8, wherein the visual feedback comprises a point counter, where the point counter is configured to increment upon identification of an SMR spindle.

10. A method for neurofeedback-triggered therapy, comprising:

conditioning a user to reduce symptoms of a neurological condition on demand by:

obtaining brain activity data from a brain activity recorder;

identifying sensorimotor rhythm (SMR) spindles in the brain activity data; and responsive to the identification of the SMR spindles, providing a therapeutic stimulation with a therapeutic effect to the user, wherein the therapeutic stimulation comprises vibrotactile Coordinated Reset (vCR) stimulation using a plurality of vibrotactile stimulators, wherein the vCR stimulation reduces the symptoms of the neurological condition of the user by desynchronizing abnormal synchrony in the user's brain, and whereby the vCR stimulation conditions the user to consciously upregulate a frequency of the SMR spindles to induce desynchronization of abnormal synchrony during a subsequent period without the vCR stimulation.

11. The method for neurofeedback-triggered therapy of claim 10, wherein the brain activity recorder is an electroencephalogram (EEG) machine.

12. The method for neurofeedback-triggered therapy of claim 11, wherein the EEG machine is integrated into a headwear.

13. The method for neurofeedback-triggered therapy of claim 10, wherein the neurological condition is selected from the group consisting of: Parkinson's disease, essential tremor, dystonia, epilepsy, dysfunction after stroke, obsessive-compulsive disorder, Tourette syndrome, dementia, depression, and complex regional pain syndrome.

14. The method for neurofeedback-triggered therapy of claim 10, wherein the plurality of vibrotactile stimulators comprises eight vibrotactile stimulators, where each stimulator is configured to be uniquely placed on fingertips of an index finger, a middle finger, a ring finger, and a pinky finger of a right and a left hand of the user.

15. The method for neurofeedback-triggered therapy of claim 14, wherein the vCR stimulation is provided in a wave-inducing stimulation sequence.

16. The method for neurofeedback-triggered therapy of claim 15, further comprising introducing a shift into the wave-inducing stimulation sequence after a predetermined number of stimulation cycles.

17. The method for neurofeedback-triggered therapy of claim 10, further comprising providing visual feedback via a display.

18. The method for neurofeedback-triggered therapy of claim 17, wherein the visual feedback comprises a point counter, where the point counter increments upon identification of an SMR spindle.

19. A neurofeedback-triggered therapy system for reducing symptoms of a neurological condition of a user, comprising:

a plurality of stimulators;

a brain activity recorder; and wherein the controller is configured to:

obtain brain activity data from the brain activity recorder;

identify SMR spindles in the brain activity data; and responsive to identification of SMR spindles, provide a therapeutic stimulation with a therapeutic effect to the user, wherein the therapeutic stimulation is provided using the plurality of stimulators, wherein the stimulation is configured to treat the symptoms of the neurological condition by desynchronizing abnormal synchrony in the user's brain, and whereby the stimulation is configured to condition the user to consciously upregulate a frequency of the SMR spindles to induce desynchronization of abnormal synchrony during a subsequent period without the vCR stimulation.

20. The system of claim 19, wherein:

the brain activity recorder is an electroencephalogram (EEG) machine;

the stimulation is Coordinated Reset stimulation delivered using a stimulation mechanism selected from the group consisting of: vibrotactile stimulation, acoustic stimulation, visual stimulation, thermal stimulation, transcutaneous electrical stimulation, transcranial electrical stimulation, and transcranial magnetic stimulation;

the stimulation is configured to treat the symptoms of the neurological condition by desynchronizing abnormal synchronizations in the user's brain; and the neurological condition is selected from the group consisting of: Parkinson's disease, essential tremor, dystonia, epilepsy, dysfunction after stroke, obsessive-compulsive disorder, Tourette syndrome, dementia, depression, and complex regional pain syndrome.

* * * * *